(12) United States Patent
Osada et al.

(10) Patent No.: US 6,818,664 B2
(45) Date of Patent: Nov. 16, 2004

(54) ANGIOGENESIS INHIBITOR

(75) Inventors: Hiroyuki Osada, Saitama (JP);
Hideaki Kakeya, Saitama (JP); Hiroshi Konno, Akita (JP); Susumu Kanazawa, Kanagawa (JP)

(73) Assignees: Riken, Saitama (JP); Institute of Biotechnology Applied to Soil Eumycetes, Tokyo (JP)

( * ) Notice: Subject to any disclaimer, the term of this patent is extended or adjusted under 35 U.S.C. 154(b) by 26 days.

(21) Appl. No.: 10/252,100

(22) Filed: Sep. 23, 2002

(65) Prior Publication Data

US 2003/0109567 A1 Jun. 12, 2003

(30) Foreign Application Priority Data

Sep. 26, 2001 (JP) ........................................ 2001-293936

(51) Int. Cl.[7] ........................ A61K 31/40; C07D 491/10
(52) U.S. Cl. ........................ 514/409; 548/410; 549/475; 514/473; 435/119
(58) Field of Search ........................ 548/410; 549/475; 514/409, 473; 435/119

(56) References Cited

PUBLICATIONS

J. Folkman, "New Perspectives in Clinical Oncology from Angiogenesis Research", *European Journal of Cancer*, vol. 34A, No. 14, pp. 2534–2539 (1996).

Judah Folkman; "Angiogenesis in Cancer, Vascular, Rheumatoid and Other Disease", *Nature Medicine,* vol. 1, No. 1, pp. 27–31 (1995).

Albert Zlotnik et al., "Chemokines: A New Classification System and Their Role in Immunity", *Immunity,* vol. 12, pp. 121–127 (2000).

J. Folkman, "New Perspectives in Clinical Oncology from Angiogenesis Research", *European Journal of Cancer*, vol. 32A, No. 14, pp. 2534–2539 (1996).

*Primary Examiner*—Joseph K. McKane
*Assistant Examiner*—Golam M M Shameem
(74) *Attorney, Agent, or Firm*—Greenblum & Bernstein, P.L.C.

(57) ABSTRACT

A compound represented by the following formula (I) or a salt thereof and a medicament such as an angiogenesis inhibitor and an antitumor agent which comprises said compound or a physiologically acceptable salt thereof as an active ingredient.

(I)

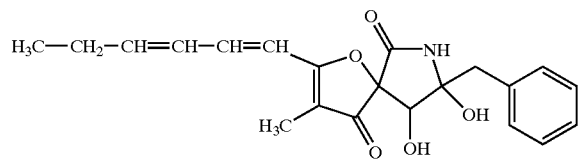

21 Claims, No Drawings

ANGIOGENESIS INHIBITOR

TECHNICAL FIELD

The present invention relates to novel compounds which are useful as active ingredients of medicaments such as angiogenesis inhibitors and antitumor agents.

BACKGROUND ART

Recently, angiogenesis has been elucidated as an important physiological phenomenon in proliferation and metastasis of various progressive solid cancers. The angiogenesis is completed through steps including, for example, (1) stimulation by vascular endothelial growth factor (VEGF) secreted from tumor cells; (2) disengagement of periheliocyte or decomposition or digestion of extracellular matrix such as basal membrane; (3) migration and proliferation of vascular endothelial cells; (4) formation of tubule by the endothelial cells, formation of basal membrane, and maturation of blood vessel. In tumorous angiogenesis, the generated new vessels have a role of supplying oxygen and nutriment to tumors to accelerate their growth and serving as a route for infiltration and metastasis of tumor cells to other tissues.

Among them, the vascular endothelial growth factor has variety of functions in the blood, vessel, and coagulation system such as for induction of proliferation and survival and maintenance of vascular endothelial cells, acceleration of blood vessel permeability, platelet migration, and chemotaxis of macrophage, as well as for angiogenesis. Therefore, novel compounds inhibiting chemotaxis that is induced by VEGF derived from vascular endothelial cells are expected to be useful as angiogenesis inhibitors, antitumor agents, agents inhibiting metastasis, and agents for treatment of rheumatic arthritis (Eur. J. Cancer, 32A, 2534–2539, 1996; Nature Med., 1, 27–31, 1995, Immunity, 12, 121, 2000).

In addition, angiogenesis inhibitors are potential therapeutic medicament for diabetic retinopathy as one of complications of diabetic vascular diseases. At present, treatments for diabetic retinopathy are given basically as symptomatic treatments, and since late treatments often result in ablepsia, effective medicaments are desired which are effective in preventive and therapeutic treatments. In recent years, angiogenesis inhibitors based on variety of modes of actions have been clinically developed. Under the circumstances, novel compounds as potential lead compounds have always been desired strongly.

DISCLOSURE OF THE INVENTION

An object of the present invention is to provide novel compounds which exert angiogenesis inhibitory activity, antitumor activity, and metastasis inhibitory activity by inhibiting chemotaxis of vascular endothelial cells. Another object of the present invention is to provide a method for preparing a novel compound having the aforementioned features and a medicament comprising said compound as an active ingredient.

The inventors of the present invention conducted various studies to achieve the foregoing objects. As a result, they found that novel compounds isolated from a culture of a microorganism belonging to genus Neosartorya, a filamentous fungus, has angiogenesis inhibitory activity and antitumor activity. The present invention was achieved on the basis of the findings.

The present invention thus provides a compound represented by the following formula (I) or a salt thereof.

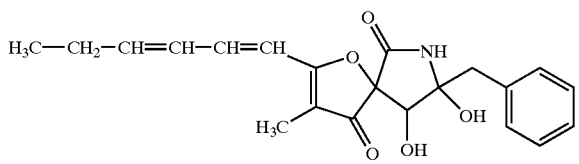

According to preferred embodiment of the invention, provided is a compound represented by the following formula (II) or a salt thereof.

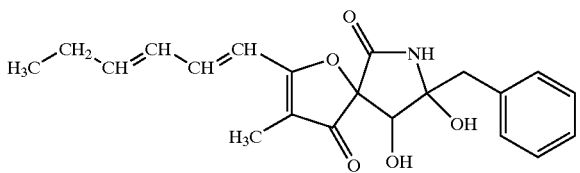

According to another aspect of the present invention, provided is a medicament which comprises the aforementioned compound or a physiologically acceptable salt thereof as an active ingredient. The medicament can be used as a medicament for preventive and/or therapeutic treatment of diseases with excess angiogenesis or diseases resulting from excess angiogenesis, therapeutic treatment of malignant tumors, inhibition of metastasis of malignant tumors, preventive and/or therapeutic treatment of diabetes and complication of diabetes, and preventive and/or therapeutic treatment of inflammatory diseases. The present invention further provides an angiogenesis inhibitor which comprises the aforementioned compound or a physiologically acceptable salt thereof as an active ingredient; an inhibitor against chemotaxis of vascular endothelial cells which comprises the aforementioned compound or a physiologically acceptable salt thereof as an active ingredient; an antitumor agent which comprises the aforementioned compound or a physiologically acceptable salt thereof as an active ingredient; and an inhibitor against metastasis of malignant tumors which comprises the aforementioned compound or a physiologically acceptable salt thereof as an active ingredient. The angiogenesis inhibitor can be administered, for example, for preventive and/or therapeutic treatment of diabetic retinopathy.

As a further aspect of the present invention, there is provided a method for preparing the aforementioned compound or a salt thereof, which comprise the step of separating and collecting the aforementioned compound or a salt thereof from a culture obtained by culturing a microorganism belonging to genus Neosartorya which can produce the aforementioned compound. The present invention also provides a method for therapeutic treatment of malignant tumors which comprises the step of administering a therapeutically effective amount of the aforementioned compound or a physiologically acceptable salt thereof to a mammal including a human; a method for inhibition of metastasis of malignant tumors which comprises the step of administering a therapeutically effective amount of the aforementioned compound or a physiologically acceptable salt thereof to a mammal including a human; a method for angiogenesis inhibition in tumor tissues which comprises the step of administering a therapeutically effective amount of the aforementioned compound or a physiologically acceptable salt thereof to a mammal including a human; a method for suppression of abnormal acceleration of angiogenesis which comprises the step of administering a therapeutically effective amount of the aforementioned compound or a physiologically acceptable salt thereof to a mammal including a human; a method for preventive and/or therapeutic treatment of diabetic retinopathy which comprises the step of administering a therapeutically effective amount of the aforementioned compound or a physiologically acceptable salt thereof to a mammal including a human; and a method for inhibition of chemotakis of vascular endpthelial cells which comprises the step of administering a therapeutically effective amount of the aforementioned compound or a physiologically acceptable salt thereof to a mammal including a human.

BEST MODE FOR CARRYING OUT THE INVENTION

The compound represented by the formula (I) or (II) according to the present invention (either or both of them are hereinafter referred to as "the compound of the present invention") has asymmetric carbon atoms, and stereoisomers such as optical isomers and diastereomers based on the asymmetric carbon atoms exist. The stereoisomers in a pure form as well as mixtures of any stereoisomers or racemates fall within the scope of the present invention. The compound of the present invention has plural olefinic double bonds, and geometrical isomers based on each double bond may exist. The geometrical isomers in a pure form as well as mixtures of any geometric isomers fall within the scope of the present invention. An example of a preferred geometrical isomer is the compound represented by the formula (II).

The compound of the present invention in a free form, as well as a salt of the aforementioned compound, preferably a physiologically acceptable salt, falls within the scope of the present invention. The form of the salt is not particularly limited. A salt such as a sodium salt may sometimes be formed with the hydroxyl groups in the molecule. A hydrate or a solvate of the aforementioned compound or a salt thereof also falls within the scope of the present invention. A preferred example of the compound of the present invention includes the compound represented by the formula (II). This particular compound may sometimes be referred to as "RKB-3134A" in the specification.

A method for preparing the compound of the present invention is not particularly limited. Examples include a method for separating and collecting the target compound from a culture of a microorganism which can produce the compound of the present invention (extracting method), or a method for chemically synthesizing the target compound by using a compound having a similar structure as a starting material which is contained in a culture of a microorganism (synthetic method or semi-synthetic method). In the extracting method, a microorganism that can produce the compound of the present invention is cultured in a medium under conditions which are used in an ordinaiy fermentation production, and then the target product can be separated and collected from the resulting culture. An example of the microorganism that can produce the compound of the present invention includes BAUA 3134 strain belonging to genus Neorsartorya. This microorganism has been deposited in Patent and Bio-Resource Center of National Institute of Advanced Industrial Science and Technology (Chuo-6, 1-1-1, Higashi, Tsukuba, Ibaraki, Japan) with the ascension number of FERM P-18455 on Aug. 13, 2001, and said deposition has been transferred to the international deposition under Budapest Treaty with the accession number of FERM BP-8189 on Sep. 19, 2002.

A medium for preparing the compound of the present invention is not particularly limited, and any of synthetic mediums or natural mediums can be suitably used so long as they appropriately contain carbon resources, nitrogen resources, and inorganic salts. If necessary, mediums may be added with vitamins and other nutrient substances.

As the carbon sources, one or more kinds of resources may suitably be chosen and used in consideration of auxotrophy of a microorganism from general carbon sources, for example, sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen sources include organic nitrogen-containing compounds such as soy bean powder, corn steep liquor, beef extract, peptone, yeast extract, amino acid mixtures, and fish powder, and inorganic nitrogen compounds such as ammonium salts and nitrates, and one or more kinds of the resources may suitably be chosen and used in consideration of auxotrophy of a microorganism. As the inorganic salt, for example, calcium carbonate, sodium chloride, potassium chloride, magnesium sulfate, cupper sulfate, manganese chloride, zinc sulfate, cobalt chloride, and various phosphates may be added, if necessary. A defoaming agent such as vegetable fats and polypropylene alcohols can also be added, if necessary.

A cultivation temperature may appropriately chosen and changed within a range that allows growth of a microorganism and production of the compound of the present invention. Preferred cultivation temperature is from 10° C. to 32° C., and more preferably from 20° C. to 28° C. Initial pH is preferably from about 6 to 8, and cultivation period of time is generally about one day to a few weeks. The cultivation may be terminated when a produced amount of the compound of the present invention reaches to that can be collected, preferably reaches to the maximum amount. A cultivation method is not particularly limited, and any method ordinarily used can be suitably used such as solid layer cultivation and normal stirring cultivation.

In order to separate and collect the compound of the present invention from the culture liquid, any technique ordinarily used for collecting microbial metabolites can be appropriately applied. Examples include chromatography with various ion exchange resins, nonionic adsorbing resins, gel filtration chromatography, or adsorbent such as activated charcoal, alumina, and silica gel, or high performance liquid chromatography, or crystallization, concentration under reduced pressure, or lyophilization, which techniques can be used alone or in appropriate combination thereof, or repeatedly.

The compound of the present invention has excellent angiogenesis inhibitory action and antitumor activity. Accordingly, the compound of the present invention is useful as an active ingredient of a medicament for preventive and/or therapeutic treatment of various diseases in which excess angiogenesis is involved as one of causes of onset thereof. The medicament of the present invention can be used for mammals including human, for example, as a medicament for preventive and/or therapeutic treatment of diabetic vascular complications, diabetic retinopathy, articular rheumatism, rheumatoid arthritis, diabetes, arteriosclerosis, ulcerative colitis, psoriasis, angiopoietic glaucoma, inflammatory diseases and the like, as well as an antitumor agent or a tumor metastasis inhibitor.

A route of administration, a dosage form, and a dose of the medicament comprising the compound of the present invention as an active ingredient can be appropriately chosen depending on a purpose of administration. For example, the route of administration of the medicament comprising the compound of the present invention as an active ingredient may be oral administration or parenteral administration. Examples of the dosage form include oral preparations such as tablets, powders, capsules, granules, extracts, and syrups, and parenteral preparations such as injections, drip infusions, and suppositories. These preparations can be manufactured according to known methods by using pharmaceutically acceptable additives such as excipients and binders. A dose of the medicament comprising the compound of the present invention as an active ingredient may usually be from about 0.1 to 1 g, preferably from about 1 mg to 100 mg, per day for oral administration for an adult, and from about 0.01 to 100 mg, preferably from about 0.1 mg to 20 mg, per day for parenteral administration for an adult, which may be increased or decreased depending on the age and body weight of a patient, type of a disease, a degree of symptom and the like. The aforementioned dose can be administered once a day or several times a day as divided portions. However, a dose out of the aforementioned range can be administered, if necessary.

When the compound of the present invention is used as a reagent, the compound can be used by dissolving in an organic solvent or a water-containing organic solvent. For example, cell growth can be inhibited by direct application to various culture cell systems. Examples of usable organic solvent include methanol, dimethyl sulfoxide and the like. Examples of reagent forms include solid preparations such as powders, or liquid preparations dissolved in an organic solvent or a water-containing organic solvent. When the aforementioned compound is used as a reagent for exerting angiogenesis inhibitory action, an effective amount is generally from 0.3 to 30 $\mu$g/ml. An appropriate amount may differ depending on a type of a culture cell system and a purpose to use the reagent, however, the amount can suitably be chosen by one of ordinary skill in the art. The amount out of the aforementioned range can be applied, if necessary.

EXAMPLES

The present invention will be explained more specifically by way of examples. However, the scope of the present invention is not limited by the following examples.

Example 1

Neosartorya BAUA3134 strain was inoculated into a medium comprising glucose 1.0%, soluble starch 2.0%, soy bean powder 1.5%, malt extract 0.5%, vegetable extract 10%, potassium diphosphate 0.05%, potato dextrose 2.6%, and magnesium sulfate 0.05%, and then cultivation was carried out with shaking at 28° C. for 72 hours. The culture (140 ml) was inoculated to a medium of the same composition (15 liters), and cultivation was carried out with shaking at 28° C. for 72 hours. The aforementioned culture was separated into bacterial mass and a supernatant by using a centrifugal separator, and the supernatant was adjusted to pH 7.3 and extracted with 15 liters of ethyl acetate. After extraction, all ethyl acetate layers were combined and concentrated under reduced pressure to give brown syrup 4.5 g.

The syrup was dissolved in chloroform 10 ml and applied to a silica gel column charged with chloroform (4 cm diameter, 60 cm length). Initially, elution was performed with chloroform 500 ml, then with each 500 ml of a chloroform/methanol solution having a successively changed mixing ratio (100:0, 100:2, 50:1, 20:1, 10:1, 5:1, 1:1). The compound of the present invention, RKB-3134A, was eluted in a fraction with the chloroform/methanol solution (50:1). The fraction was concentrated under reduced pressure to give a brown syrup 1.4 g. Then, the brown syrup 1.4 g was dissolved in a methanol/acetonitrile solution (1:1, 14 ml) and made into aliquots, and purified by high performance liquid chromatography (acetonitrile : water=2:8→acetonitrile: water=1:1; linear gradient (30 minutes), flow rate 9.0 ml/min) using a reverse phase ODS column (2 cm diameter, 25 cm length, PEGASIL ODS, Senshu Kagaku Co.) to give RKB-3134A. Recrystallization was further carried out from a mixed solvent of hexane/ethyl acetate/methanol to give a pure RKB-3134A (90 mg) as pale yellow powder. Physicochemical properties of RKB-3134A are shown below.

Appearance: pale yellow powder
Melting point: 166–167° C.
Specific rotation: −204.4 (c=0.158, 25° C., methanol)
Molecular formula: $C_{21}H_{23}NO_5$
High-resolution mass spectrum (HR-FABMS): $(M+H)^+$
Found (m/z): 370.1683
Calcd.(m/z): 370.1654
UV $\lambda$ max nm (methanol) ($\epsilon$): 231(5900), 342(27860)
IR $\nu$ max (KBr) $cm^{-1}$: 3570, 2975, 1735, 1715, 1705, 1675, 1610, 1410, 1135, 700
$R_f$ value (Silica gel 60 $F_{254}$, Merck): 0.50 (developing solvent; hexane : ethyl acetate=1:1), 0.34 (developing solvent; chloroform : methanol=40:1)
Color reaction (positive): 10% sulfuric acid
Solubility: easily soluble in methanol, acetone, or dimethyl sulfoxide. Insoluble in n-hexane or water.

NMR data of RKB-3134A is shown in Table 1 (solvent: dimethyl sulfoxide-$d_6$, $\delta$ ppm, internal standard: TMS, $^{13}C$: 125 MHz, $^1H$: 500 MHz).

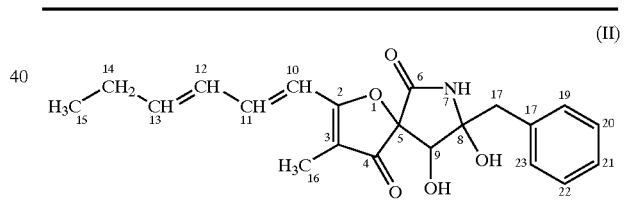

(II)

| position | $^{13}C$ (multiplet) | $^1H$ (multiplet) | (J/Hz) |
| --- | --- | --- | --- |
| 1 | | | |
| 2 | 181.46 s | | |
| 3 | 110.25 s | | |
| 4 | 198.93 s | | |
| 5 | 93.54 s | | |
| 6 | 164.80 s | | |
| 7 | | | |
| 8 | 85.36 s | | |
| 9 | 71.09 d | 4.09 d | 5.4 |
| 10 | 115.08 d | 6.60 d | 15.2 |
| 11 | 140.69 d | 7.16 dd | 10.5, 15.2 |
| 12 | 128.38 d | 6.34 dd | 10.5, 15.2 |
| 13 | 147.47 d | 6.42 dt | 15.2, 6.2 |
| 14 | 25.59 t | 2.18 m | |
| 15 | 12.61 q | 0.99 d | 7.3 |
| 16 | 5.22 q | 1.68 s | |
| 17 | 40.43 t | 2.94 d | 14.0 |
| | | 3.01 d | 14.0 |
| 18 | 135.80 s | | |
| 19, 23 | 130.78 d | 7.36 dd | 1.2, 7.6 |
| 20, 22 | 128.13 d | 7.34 dd | 6.7, 7.6 |
| 21 | 126.83 d | 7.29 dd | 1.2, 6.7 |
| 8-OH | | 5.87 br. s | |
| 9-OH | | 6.19 d | 5.4 |

-continued

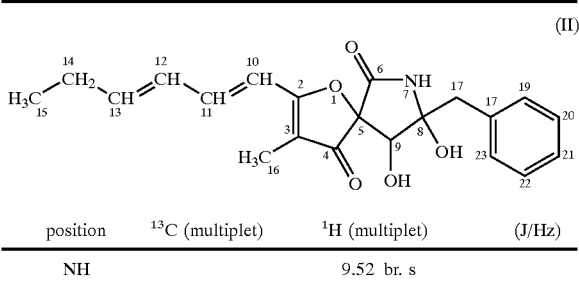

| position | $^{13}$C (multiplet) | $^1$H (multiplet) | (J/Hz) |
|---|---|---|---|
| NH | | 9.52 br. s | |

Test Example 1: Inhibition of chemotaxis of vascular endothelial cells by RKB-3134A HUVEC cells, normal human unbilical vein vascular endothelial cells maintained in HuMedia-EG2 (KURABO) medium, were inoculated on the upper layer of a three-dimensional culture using a chemotaxel chamber. HuMedia-EG2 containing vascular endothelial cell growth factor (VEGF) was charged in the lower layer to induce chemotaxis of HUVEC cells. RKB-3134A inhibited chemotaxis of HUVEC cells induced by VEGF in the concentration of from 1 to 30 μg/ml. These results indicate that RKB-3134A exerts chemotaxis inhibitory action of vascular endothelial cells based on its anti-VEGF action and that the compound of the present invention is effective as an angiogenesis inhibitor, an antitumor agent, a tumor metastasis inhibitor and the like.

Preparation Example 1

Injection and Drip Infusion

RKB-3134 A was aseptically divided and sealed in vials so as to contain 10 mg of the compound with powder glucose 5 g, and the vials were charged with an inert gas such as nitrogen or helium and stored in a cool and dark place. The preparation can be dissolved in ethanol and added with 0.85% physiological saline (100 ml) before use to prepare an intravenous injection and administered by intravenous injection or drip infusion in the amount of from 10 to 100 ml per day depending on symptoms.

Preparation Example 2

Granules

RKB-3134A (1 g), lactose (98 g), and hydroxypropyl cellulose (1 g) were measured and well mixed, and then formed into particles according to a conventional method. The resulting product was well dried to prepare granules suitable for a package in a bottle or a heat seal container. The preparation can be orally administered in a dose of 100 to 1,000 mg per day depending on symptoms.

The compound of the present invention has inhibitory action on chemotaxis of vascular endothelial cells and exerts angiogenesis inhibitory action. The compound of the present invention is useful as an active ingredient of a medicament for preventive and/or therapeutic treatment of various diseases in which excess angiogenesis is involved as one of causes of onset thereof, such as diabetic retinopathy, articular rheumatism, and tumors.

The present disclosure relates to subject matter contained in priority Japanese Patent Application No. 2001-293936, filed on Sep. 26, 2001, the contents of which is herein expressly incorporated by reference in its entirety.

What is claimed is:
1. A compound represented by the following formula (I) or a salt thereof:

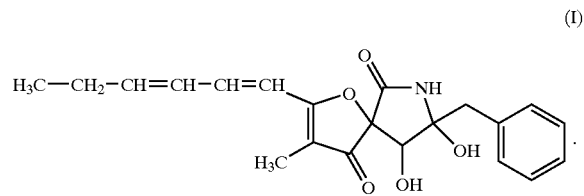

2. A compound represented by the following formula (II) or a salt thereof:

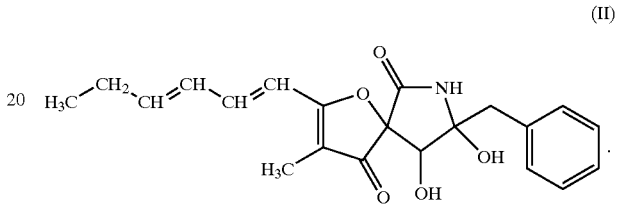

3. A pharmaceutical composition which comprises the compound according to claim 1 or a physiologically acceptable salt thereof as an active ingredient, and a pharmaceutically acceptable additive.

4. A pharmaceutical composition which comprises the compound according to claim 2 or a physiologically acceptable salt thereof as an active ingredient, and a pharmaceutically acceptable additive.

5. The pharmaceutical composition according to claim 3, which is an angiogenesis inhibitor.

6. The pharmaceutical composition according to claim 3, which is an antitumor agent.

7. The pharmaceutical composition according to claim 3 for therapeutic treatment of diabetes.

8. The pharmaceutical composition according to claim 3, for therapeutic treatment of an inflammatory disease.

9. The pharmaceutical composition according to claim 4, which is an angiogenesis inhibitor.

10. The pharmaceutical composition according to claim 4, which is an antitumor agent.

11. The pharmaceutical composition according to claim 4 for therapeutic treatment of diabetes.

12. The pharmaceutical composition according to claim 4 for therapeutic treatment of an inflammatory disease.

13. A method for preparing the compound or the salt thereof according to claim 1, which comprise separating and collecting the compound or the salt thereof according to claim 1 from a culture obtained by culturing a microorganism which belongs to genus Neosartorya capable of producing said compound.

14. A method for therapeutic treatment of diabetes comprising administering to a mammal a therapeutically effective amount of the compound according to claim 1 or a physiologically acceptable salt thereof.

15. The method according to claim 14, wherein the mammal is a human.

16. A method for therapeutic treatment of an inflammatory disease comprising administering to a mammal a therapeutically effective amount of the compound according to claim 1 or a physiologically acceptable salt thereof.

17. The method according to claim 16, wherein the mammal is a human.

18. A method for therapeutic treatment of diabetes comprising administering to a mammal a therapeutically effective amount of the compound according to claim 2 or a physiologically acceptable salt thereof.

19. The method according to claim 18, wherein the mammal is a human.

20. A method for therapeutic treatment of an inflammatory disease comprising administering to a mammal a therapeutically effective amount of the compound according to claim 2 or a physiologically acceptable salt thereof.

21. The method according to claim 20, wherein the mammal is a human.

\* \* \* \* \*